US010206636B2

United States Patent
Hayashi

(10) Patent No.: US 10,206,636 B2
(45) Date of Patent: Feb. 19, 2019

(54) X-RAY DIAGNOSTIC APPARATUS

(71) Applicant: Toshiba Medical Systems Corporation, Otawara-shi (JP)

(72) Inventor: Yoshiyasu Hayashi, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 420 days.

(21) Appl. No.: 15/179,360

(22) Filed: Jun. 10, 2016

(65) Prior Publication Data

US 2016/0361034 A1 Dec. 15, 2016

(30) Foreign Application Priority Data

Jun. 11, 2015 (JP) .................................. 2015-118398

(51) Int. Cl.
*A61N 5/10* (2006.01)
*B25J 9/16* (2006.01)
*A61B 6/10* (2006.01)
*A61B 6/00* (2006.01)

(52) U.S. Cl.
CPC ............ *A61B 6/102* (2013.01); *A61B 6/4014* (2013.01); *A61B 6/4441* (2013.01)

(58) Field of Classification Search
CPC .......... A61N 2005/1061; A61N 5/1049; A61N 5/1069; A61N 5/01; A61N 2005/1063; A61N 2005/1097; A61B 6/032
See application file for complete search history.

(56) References Cited

U.S. PATENT DOCUMENTS

| 4,884,293 | A | 11/1989 | Koyama |
| 10,010,720 | B2 * | 7/2018 | Cheng .................. A61N 5/1049 |
| 2015/0342557 | A1 | 12/2015 | Kojima et al. |

FOREIGN PATENT DOCUMENTS

| JP | 1-185246 A | 7/1989 |
| JP | 2001-137222 A | 5/2001 |
| JP | 2004-275745 | 10/2004 |
| JP | 2007-268060 A | 10/2007 |
| JP | 2009-60953 A | 3/2009 |
| JP | 2014-151085 A | 8/2014 |

* cited by examiner

Primary Examiner — Don Wong
(74) Attorney, Agent, or Firm — Oblon, McClelland, Maier & Neustadt, L.L.P.

(57) ABSTRACT

According to one embodiment, an X-ray diagnostic apparatus includes a first apparatus, a second apparatus, movement instruction input circuitry and control circuitry. In accordance with a movement instruction, the control circuitry is configured to control the first and second apparatuses so that the first apparatus can be moved to the target position. The control circuitry is configured to perform a retraction operation and a restoration operation. The retraction operation is an operation in which the first apparatus starts moving toward the target position and continues to move toward the target position, with the second apparatus retracted. The restoration operation is an operation in which the second apparatus is returned to the original position while avoiding the collision with the first apparatus.

20 Claims, 4 Drawing Sheets

| Priority | Apparatus |
|---|---|
| 1 | First arm, second arm |
| 2 | Monitor table |
| 3 | Bed, top plate |
| 4 | |
| 5 | |
| 6 | |
F I G. 4
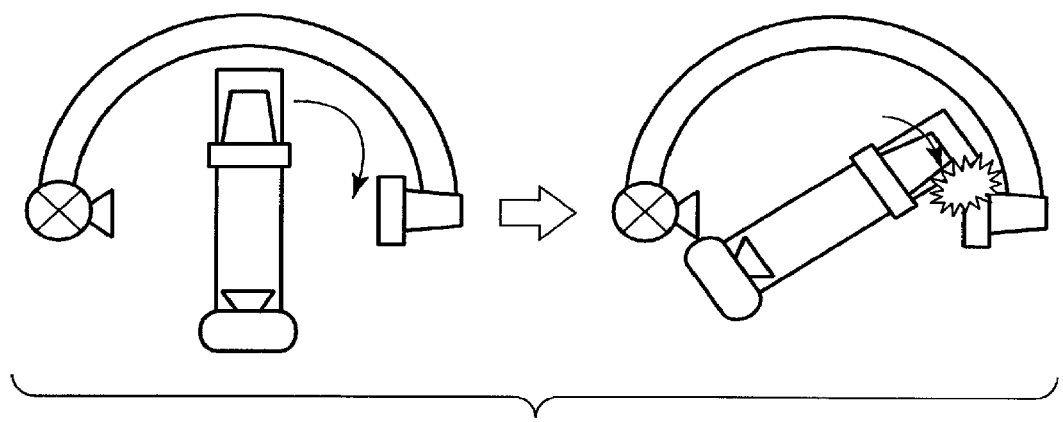
F I G. 5

X-RAY DIAGNOSTIC APPARATUS

CROSS-REFERENCE TO RELATED APPLICATIONS

This application is based upon and claims the benefit of priority from prior Japanese Patent Application No. 2015-118398, filed on Jun. 11, 2015, the entire contents of which are incorporated herein by reference.

FIELD

Embodiments described herein relate to an X-ray diagnostic apparatus.

BACKGROUND

In a biplane X-ray diagnostic apparatus, interference control is performed for preventing collision of arms. FIG. 5 is a schematic diagram illustrating interference control. When a first arm moves and enters the region within a predetermined distance of a second arm, the interference control is performed. For example, deceleration, alarm notification, etc., are performed.

In known interference control, when a first arm is moved, a second arm moves, interlocking with the first arm, and a certain relative angle between the first and second arms is maintained to prevent interference between the arms. In other known interference control, when a first arm is moved, a second arm is partly retracted to reduce the possibility of interference.

In interference control, after the end of the movement of the first arm, the second arm interlocking with the first arm has to be manually moved to a predetermined position so that it does not become an obstacle to the first arm.

BRIEF DESCRIPTION OF THE DRAWINGS

FIG. 4 shows an example of a priority table applicable to the present embodiment.

FIG. 5 is a schematic diagram illustrating the conventional interference control.

DETAILED DESCRIPTION

According to one embodiment, an X-ray diagnostic apparatus comprises a first apparatus, a second apparatus, movement instruction input circuitry and control circuitry. The first apparatus is located in an examination room and used for X-ray diagnosis. The second apparatus is located in the examination room and used for X-ray diagnosis. The movement instruction input circuitry is configured to input a movement instruction for moving the first apparatus to a target position. The control circuitry is configured to control the first and second apparatuses so that the first apparatus can be moved to the target position. The control circuitry is configured to perform a retraction operation and a restoration operation as well. The retraction operation is a retraction operation in which the first apparatus starts moving toward the target position in response to the movement instruction and continues to move toward the target position, with the second apparatus retracted. The restoration operation is an operation in which the second apparatus is returned to the original position while avoiding the collision with the first apparatus.

An X-ray diagnostic apparatus according to the present embodiment will be described with reference to the accompanying drawings. In the description below, structural elements having substantially the same functions and configurations will be denoted by the same reference symbols, and a repetitive description of such structural elements will be given only where necessary.

For the sake of simplicity, it is assumed that the X-ray diagnostic apparatus of the present embodiment is a biplane type X-ray diagnostic apparatus. The X-ray diagnostic apparatus is provided in the examination room. Needless to say, the X-ray diagnostic apparatus need not be a biplane type and may be any other type of X-ray diagnostic apparatus.

An imaging mechanism 10 comprises a first apparatus 11 and a second apparatus 13. The first apparatus 11 and the second apparatus 13 are, for example, arms, monitor tables, top plates, beds, various support members, foot switches, etc. Although it is assumed that the first apparatus 11 and the second apparatus 13 are arms to simplify the descriptions below, they may be X-ray computed tomography (CT) apparatuses or magnetic resonance imaging (MRI) apparatuses.

Figure 1:
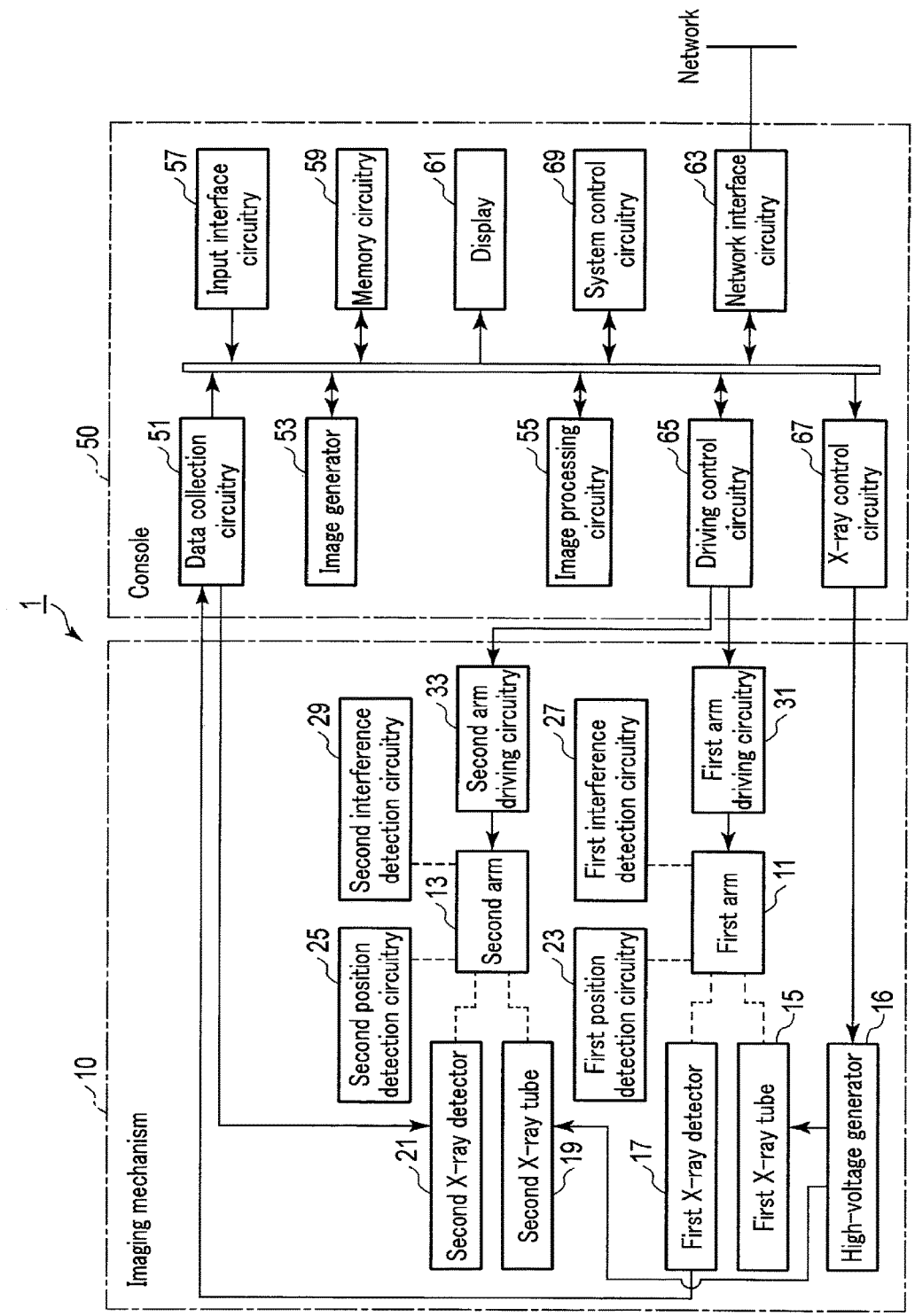
FIG. 1 is a block diagram illustrating the configuration of an X-ray diagnostic apparatus according to the present embodiment.

FIG. 1 is a block diagram illustrating the configuration of the X-ray diagnostic apparatus of the present embodiment. The X-ray diagnostic apparatus 1 comprises an imaging mechanism 10 and a console 50. The first arm 11 and the second arm 13 are made of a metal, a reinforced plastic material, or the like. The first arm 11 supports a first X-ray tube 15 and a first X-ray detector 17 in such a manner that the first X-ray tube 15 and the first X-ray detector 17 are movable while facing each other. Applied with a high voltage and supplied with a filament current from a high-voltage generator 16, the first X-ray tube 15 generates X-rays. The first X-ray detector 17 is realized, for example, by a flat panel detector (FPD). The FPD includes a plurality of pixels arranged in a two-dimensional manner. Each of the pixels detects an X-ray generated by the first X-ray tube 15 and converts the detected X-ray into an electric signal. The first X-ray detector 17 supplies the electric signal obtained by the conversion to a data collection circuitry 51. The second arm 13 supports a second X-ray tube 19 and a second X-ray detector 21 in such a manner that the X-ray tube 19 and the second X-ray detector 21 are rotatable while facing each other. Applied with a high voltage and supplied with a filament current from the high-voltage generator 16, the second X-ray tube 19 generates X-rays. The second X-ray detector 21 is realized, for example, by a flat panel detector (FPD). The FPD includes a plurality of pixels arranged in a two-dimensional manner. Each of the pixels detects an X-ray generated by the second X-ray tube 19 and converts the detected X-ray into an electric signal. The second X-ray detector 21 supplies the electric signal obtained by the conversion to the data collection circuitry 51.

More specifically, the first arm 11 is a frontal arm 11 (hereinafter referred to as an F-side arm), and the second arm 13 is a lateral arm 13 (hereinafter referred to as an L-side arm). The F-side arm 11 and the L-side arm 13 are interchangeable with each other.

The first arm 11 is provided with first position detection circuitry 23. The first position detection circuitry 23 detects the position of the first arm 11. The position of the first arm 11 is defined, for example, as an angle around the axis of rotation. Where the first apparatus 11 is a bed or a top plate, it is defined as being at a horizontal position. The definition of a position varies depending upon the type of each device. The first position detection circuitry 23 is realized, for example, as a position sensor, a magnetic sensor, a global positioning system or the like. The first position detection circuitry 23 detects, for example, the position of the tip end of the first arm 11. Likewise, the second arm 13 is provided with second position detection circuitry 25. The second position detection circuitry 25 detects the position of the second arm 13. The position of the second arm 13 is defined, for example, as an angle around the axis of rotation. Where the second apparatus 13 is a bed or a top plate, it is defined as being at a horizontal position. The definition of a position varies depending upon the type of each device. The second position detection circuitry 25 is realized, for example, as a position sensor or the like. The second position detection circuitry 25 detects, for example, the position of the tip end of the second arm 13.

The first arm 11 is provided with first interference detection circuitry 27. The first interference detection circuitry 27 detects interference which the first arm 11 may undergo by other devices. To be specific, the first interference detection circuitry 27 is realized, for example, as a position sensor or the like. The first position detection circuitry 23 detects, for example, the second arm 13 when the second arm 13 enters the region within a predetermined range of the first arm 11 (the region will be hereinafter referred to as an interference region). The first interference detection circuitry 27 and the second interference detection circuitry 29 detect whether or not there is an obstacle between the position where the second arm 13 is detected (the original position where the second arm 13 is located before the retraction operation is performed) and the position of the second arm 13 is located when the first arm 11 has reached the target position. The "original position where the second arm 13 is located before the retraction operation" may be referred to simply as the "position before retraction." Utilizing the interference which the first arm 11 undergoes by other devices, the first interference detection circuitry 27 detects whether or not there is an obstacle. Likewise, the second interference detection circuitry 29 detects interference which the second arm 13 may undergo by other devices. To be specific, the second interference detection circuitry 29 is realized, for example, as a position sensor or the like. The second interference detection circuitry 25 detects whether there is an obstacle between the first arm 11 and the second arm 13 when the second arm 13 reaches the target position. Utilizing the function of detecting the interference which the second arm 13 undergoes by other devices, the second interference detection circuitry 29 detects whether or not there is an obstacle. The second position detection circuitry 25 detects, for example, the first arm 11 when the first arm 11 enters the interference region of the second arm 13.

Under the control of driving control circuitry 65 (to be mentioned below), first arm driving circuitry 31 generates a driving force for rotating the first arm 11. The first arm 11 is rotated by the driving force supplied from the first arm driving circuitry 31. The first arm driving circuitry 31 is realized, for example, by a motor such as a servo motor. Under the control of the driving control circuitry 65, second arm driving circuitry 33 generates a driving force for rotating the second arm 13. The second arm 13 is rotated by the driving force supplied from the second arm driving circuitry 33. The second arm driving circuitry 33 is realized, for example, by a motor such as a servo motor.

The X-ray diagnostic apparatus of the present embodiment comprises not only the imaging mechanism 10 described above but also a control 50. The console 50 comprises data collection circuitry 51, image generator 53, image processing circuitry 55, input interface circuitry 57, memory circuitry 59, a display 61, network interface circuitry 63, driving control circuitry 65, X-ray control circuitry 67 and system control circuitry 69.

The data collection circuitry 51 reads an electric signal from each of the pixels of the first X-ray detector 17 and generates digital data by digital conversion of the read electric signal. The data collection circuitry 51 is realized, for example, by a combination of a memory and a processor for executing a program. To be more specific, the data collection circuitry 51 comprises an I-V converter for converting the electric signal at each of the pixels of the first X-ray detector 17 into a voltage signal, an integrator for periodically integrating the voltage signal in synchronism with the irradiation period of an X-ray, an amplifier for amplifying the output signal of the integrator, and an analog-to-digital converter for converting the output signal of the amplifier into a digital signal. The data collection circuitry 51 supplies digital data to the image generator 53. The data collection circuitry 51 reads an electric signal from each of the pixels of the second X-ray detector 21 and generates digital data by digital conversion of the read electric signal. To be more specific, the data collection circuitry 51 comprises an I-V converter for converting the electric signal at each of the pixels of the second X-ray detector 21 into a voltage signal, an integrator for periodically integrating the voltage signal in synchronism with the irradiation period of an X-ray, an amplifier for amplifying the output signal of the integrator, and an analog-to-digital converter for converting the output signal of the amplifier into a digital signal. The data collection circuitry 51 supplies digital data to the image generator 53.

The image generator 53 performs preprocessing (such as logarithm conversion) for the digital data output from the data collection circuitry 51, thereby generating an X-ray image. The image generator 53 supplies the generated X-ray image to the memory circuitry 59.

The image processing circuitry 55 performs image processing for the X-ray image generated by the image generator 53. The data processing circuitry 55 is realized, for example, by a combination of a memory and a processor for executing a program. The image processing circuitry 55 performs processing for correcting an artifact or the like.

The input interface circuitry 57 receives various instructions, commands, information, selections, settings, etc., entered by the operator, and supplies them to the system control circuitry 69. For example, the input interface circuitry 57 receives an instruction which the operator enters for moving the first arm 11 to a target position. The input interface device is realized, for example, by a track ball, a switch button, a mouse, a keyboard or the like.

The memory circuitry 59 stores instructions entered by the operator and supplied from the input interface circuitry 57. The memory circuitry 59 stores various kinds of data. The memory circuitry 59 may store X-ray images generated by the image generator 53. The X-ray images stored in the memory circuitry 59 are supplied to the display 61, the network interface circuitry 63, etc., at proper times.

The display 61 displays various kinds of information on a monitor. For example, the display displays an X-ray image generated by the image generator 53. The display 61 may display an arbitrary image selected from the images stored in the memory circuitry 59.

The network interface circuitry 63 is connected to picture archiving and communication systems (PACS) (not shown) and to another computer, by way of a network.

The driving control circuitry 65 controls the first arm 11 and the second arm 13 so as to move the first arm 11 to a target position in response to a movement instruction which the operator enters from the input interface circuitry 57. The driving control circuitry 65 is realized, for example, by a combination of a memory and a processor for executing a program. After the first arm 11 starts moving toward the target position in response to the movement instruction, the driving control circuitry 65 causes the second arm 13 to execute the automatic retraction function. When the first arm 11 reaches the target position, the driving control circuitry 65 causes the second arm 13 to execute the automatic restoration function.

The X-ray control circuitry 67 controls the high-voltage generator 16 in accordance with an instruction supplied from the system control circuitry 69. The X-ray control circuitry 67 is realized, for example, by a combination of a memory and a processor for executing a program.

The system control circuitry 69 serves as the nerve center of the X-ray diagnostic apparatus 1. The system control circuitry 69 is realized, for example, by a combination of a memory and a processor for executing a program. The system control circuitry 69 performs overall control of the structural elements of the X-ray diagnostic apparatus 1 and enables the operations related to the present embodiment (namely, the automatic retraction function and automatic restoration function).

Figure 2:
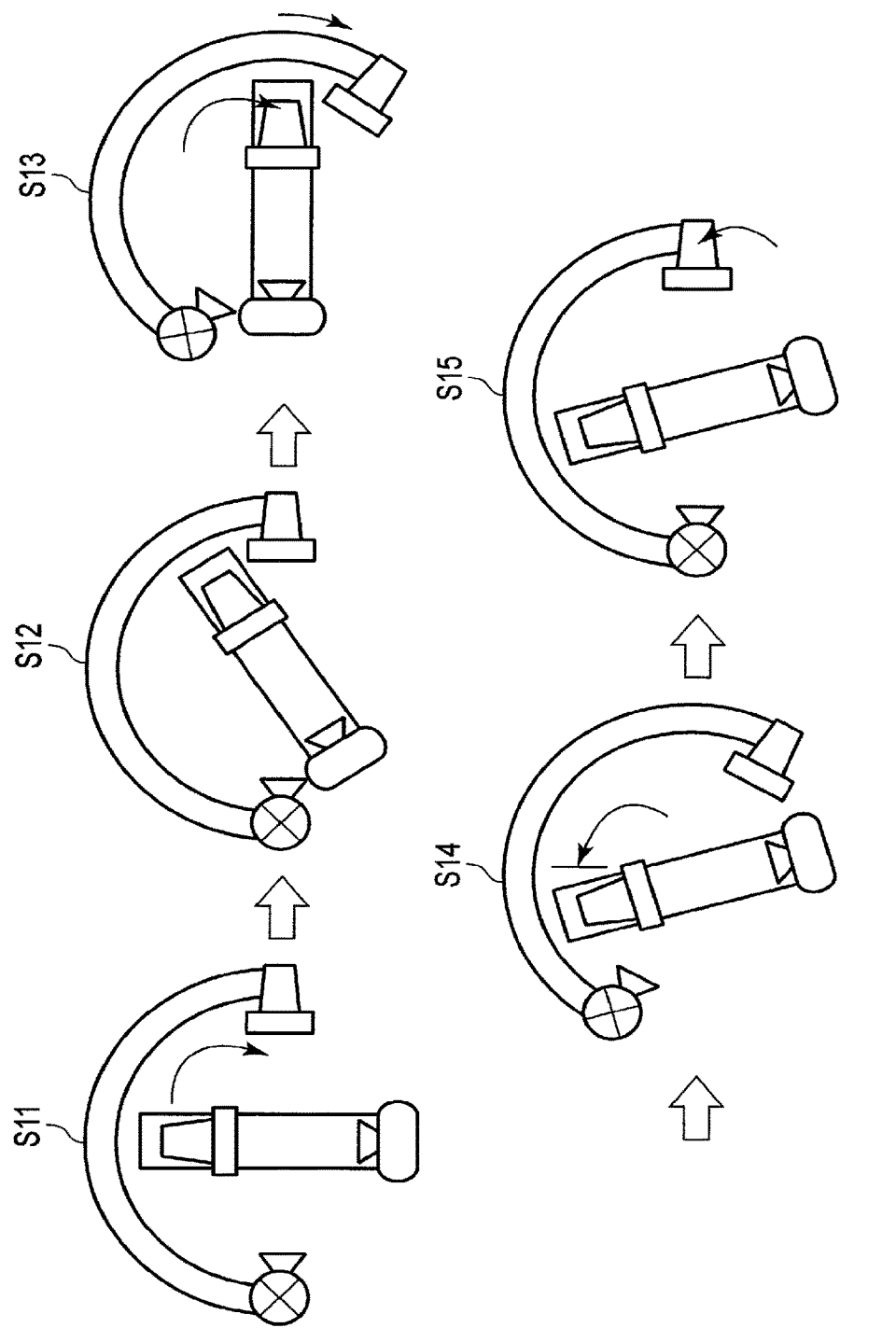
FIG. 2 schematically illustrates the automatic retraction function and automatic restoration function according to the present embodiment.

The automatic retraction function and automatic restoration function according to the present embodiment will be described with reference to FIG. 2. FIG. 2 schematically illustrates the automatic retraction function and automatic restoration function according to the present embodiment.

When the first arm 11 is rotated, the second interference detection circuitry 29 can detect whether the first arm 11 enters the interference region. When the first arm is rotated (state S11) and reaches the interference region of the second arm 13, the system control circuitry 69 controls the driving control circuitry 65 to start the automatic retraction function of the second arm 13 (state S12). When the automatic retraction function of the second arm 13 is started in state S12, the first arm 11 continues to move toward the target position, with the second arm 13 retracted. The retraction operation of the second arm 13 will be referred to as an automatic retraction function. The automatic retraction function enables the first arm 11 to be moved to the target position without consideration of the collision with the second arm 13. An apparatus that can be moved independently without reference to other apparatuses (such as a monitor table) is retracted to a predetermined position stored in the memory circuitry 59.

When the first arm 11 has been moved to the target position by the automatic retraction function (state S13), the second arm 13 may be operable and can return to the original position (state S14). If this is the case, the system control circuitry 69 controls the driving control circuitry 65 to return the second arm 13 to the original position (state S15). The operation of moving the second arm 13 to the original position will be referred to as an automatic restoration function. Since the automatic restoration function enables the second arm to move from the retracted position and return to the original position, the second arm does not become an obstacle when the first arm 11 is moved next.

Figure 3:
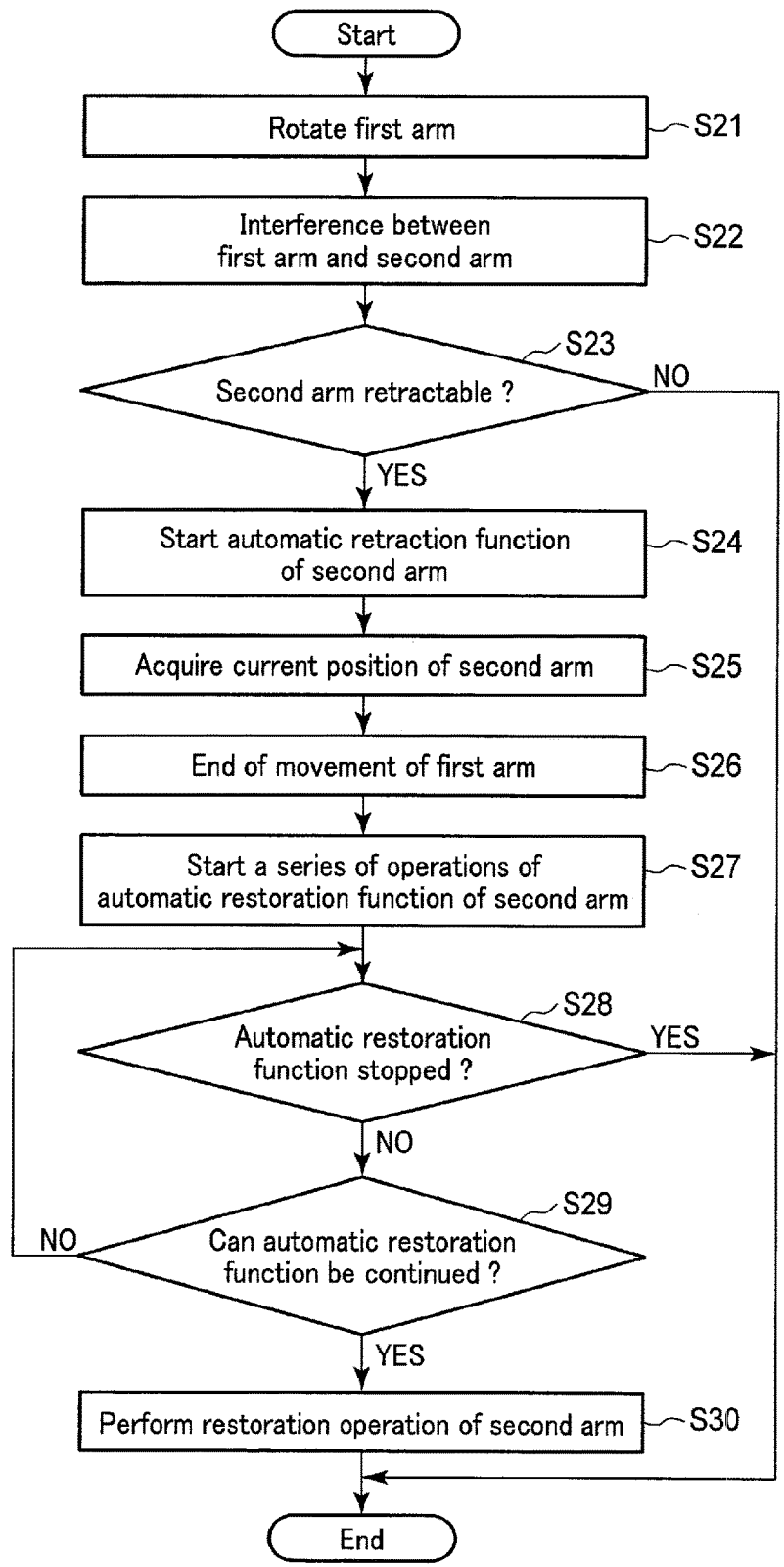
FIG. 3 is a flowchart illustrating a typical flow of the automatic retraction function and automatic restoration function according to the present embodiment.

A series of operations according to the present embodiment will be described with reference to FIG. 3. FIG. 3 is a flowchart illustrating a typical flow of the automatic retraction function and automatic restoration function according to the present embodiment. When the first arm 11 is rotated, the second interference detection circuitry 29 can detect whether the first arm 11 enters the interference region.

First of all, the system control circuitry 69 controls the driving control circuitry 65 to rotate the first arm 11 (step S21).

After step S21, the system control circuitry 69 controls the second interference detection circuitry 29 to detect whether or not the first arm 11 has entered the interference region. The first arm 11 is determined as having entered the interference region when it moves into a region within a predetermined distance of the second arm 13 (step S22).

After step S22, the system control circuitry 69 controls the driving control circuitry 65 to determine whether the second arm 13 can be retracted (step S23). In step S23, when the first arm 11 has moved close to the interference region of the second arm 13, the driving control circuitry 65 determines whether the second arm 13 can be retracted from the position acquired in step S25 (described below), while simultaneously allowing the first arm 11 to continue to move toward the target position. If the second arm 13 to be retracted interferes with another apparatus and cannot be moved, the retraction operation cannot be performed. A support member or a monitor located within an irradiation field table cannot be retracted during the execution of irradiation. The memory circuitry 59 may store data on the priority association regarding the respective apparatuses and members. FIG. 4 shows an example of a priority table applicable to the present embodiment. The priority association of the respective apparatuses and members will be described. If the priority of the second apparatus is higher than that of the first apparatus, the second apparatus does not execute the automatic restoration function. Conversely, if the priority of the second apparatus is equal to or lower than that of the first apparatus, the second apparatus executes the restoration function. In other words, the priorities indicate that the restoration cannot be executed if the priority of the second apparatus is higher than that of the first apparatus and can be executed when the priority of the second apparatus is equal to or lower than that of the first apparatus. To be specific, where the monitor table is to be moved, the first arm having higher priority than that of the monitor table is not moved. Conversely, where the first arm is to be moved, the monitor table having lower priority than that of the first arm is moved. The apparatus or member that must not be moved in any case has the highest priority. When the first apparatus starts moving in response to a movement instruction and reaches a position within a predetermined distance of the second apparatus, the driving control circuitry 65 retracts the second apparatus while maintaining the predetermined distance with reference to the first apparatus. When the first apparatus reaches the target position, the driving control circuitry 65 controls the second apparatus in accordance with the priorities described above.

After step S23, the system control circuitry 69 controls the driving control circuitry 65 to execute the automatic retraction function of the second arm 13 (step S24). After the automatic retraction function of the second arm 13 is started in step S24, the first arm 11 continues to move toward the target position, with the second arm 13 retracted.

When the automatic retraction function is started in step S24, the system control circuitry 69 controls the second position detection circuitry 25 to acquire the current position of the second arm 13 (step S25).

When the first arm 11 reaches the target position after step S25, the first arm 11 stops moving (step S26).

After step S26, the system control circuitry 69 controls the driving control circuitry 65 to start a series of operations of the automatic restoration function of the second arm 13 (step S27). In step S27, the driving control circuitry 65 confirms that the first arm 11 stops moving and controls the second arm 13 to perform a restoration operation, by which the second arm 13 is returned to the position detected in step S25. Where an X-ray tube is not performing irradiation or is not ready for irradiation, the driving control circuitry 65 controls the second arm 13 in such a manner that the second arm 13 is returned to the position acquired in step S25.

After step S27, the input interface circuitry 57 is on standby, waiting for an operator's instruction for stopping the automatic restoration function (step S28). In step S28, executed after the start of the automatic restoration function of the second arm 13, the input interface circuitry 57 is on standby, waiting for an instruction for stopping the automatic restoration function. If an instruction for stopping the automatic restoration function is entered by the operator in step S28, a series of operations are ended. Thereafter, the driving control circuitry 65 returns the second arm 13 to the position where the second arm was located when the restoration operation was started. Alternatively, the driving control circuitry 65 may permit the second arm 13 to remain on the spot. A stopping instruction is not necessarily entered by the operator; it may be automatically issued when the second arm is irradiated with X-rays. Whether the automatic stopping instruction should be issued or not may be determined by a setting.

In the case of "NO" in step S28, the system control circuitry 69 determines whether the automatic restoration function can be continued (Step S29). In the case of "NO" in step S29, the control flow returns to step S28. If the X-ray tube emits X-rays after the second arm 13 starts the automatic restoration function, the automatic restoration function is disabled, and the second arm 13 is caused to remain on the spot.

In the case of "YES" in step S29, the system control circuitry 69 controls the driving control circuitry 65 to perform the restoration operation of the second arm 13 (step S30). In step S30, the driving control circuitry 65 returns the second arm 13 to the position acquired in step S25, following the same route as has been used. The "position acquired in step S25" may be referred to simply as the "position before retraction." When the first arm has reached the target position, the second arm 13 can move to the position acquired in step S25, following different routes. The driving control circuitry 65 may calculate times corresponding to such routes. In other words, the driving control circuitry 65 may calculate times corresponding to a plurality of routes through which the second arm 13 can move from the position where it is located when the first arm 11 has reached the target position to the position where the second arm is located before retraction. The times corresponding to a plurality of routes can be measured based on the moving distances of the respective routes and the moving speed. The driving control circuitry 65 determines which route requires the shortest time. The driving control circuitry 65 automatically returns the second apparatus to the original position, using the route requiring the shortest time.

As described above, the X-ray diagnostic apparatus of the present embodiment provides the automatic retraction function, which is enabled when the first apparatus 11 is moved to a position within a predetermined distance of the second apparatus 13 and by which the first apparatus 11 is allowed to continue to move toward the target position, with the second apparatus retracted. The automatic retraction function enables the first arm 11 to be moved to the target position without consideration of the interference between the first apparatus 11 and the second apparatus 13. In addition, the X-ray diagnostic apparatus of the present embodiment provides the automatic restoration function, which is enabled when the first apparatus 11 reaches the target position and by which the second apparatus is returned to the position acquired by the position detection circuitry. Since the automatic restoration function enables the second apparatus to move from the retracted position and return to the original position, the second apparatus does not become an obstacle when the first apparatus 11 is operated next. As described above, the present embodiment provides an X-ray diagnostic apparatus that enables efficient operations and manipulations.

The present embodiment is not limited to the structure described above.

For example, the first position detection circuitry 23 and the second position detection circuitry 25 are not necessarily required; they may be omitted, if so desired. Where the first position detection circuitry 23 and the second position detection circuitry 25 are omitted, the first arm 11 and the second arm 13 are rotated in parallel by the same angle in a retraction operation. The angle by which the first arm 11 and the second arm 13 are rotated in the retraction operation (namely, the difference between the states before and after the retraction operation) is recorded. In the restoration operation, the second arm may be returned in such a manner as to cancel the recorded angle when the first arm 11 is moved more than the recorded angle is canceled.

The restoration operation is not limited to the operation of returning the second apparatus to the position where the second apparatus is located before retraction. For example, the restoration operation includes an operation for temporarily stopping the second apparatus at a position close to the position before retraction and an operation of returning the second apparatus to the position before retraction. In other words, the restoration operation includes an operation in which the second apparatus is returned to the position before retraction while avoiding the collision with the first apparatus.

The restoration operation may be performed during the retraction operation or after the retraction operation, as long as the collision between the first apparatus and the second apparatus is prevented. For example, the restoration operation need not be executed when the first apparatus 11 has reached the target position; the restoration operation may be started when the first apparatus and the second apparatus satisfy predetermined conditions. The predetermined conditions include the condition where the collision between the first apparatus 11 and the second apparatus 13 is prevented. The predetermined conditions may include the condition where the current position of the first apparatus 11 is not located between the current position of the second apparatus 13 and the position before retraction. The predetermined conditions may include the condition where the distance between the first apparatus 11 and the second apparatus 13 exceeds a predetermined value. The predetermined conditions may include the condition where, in a retraction operation, the first arm 11 and the second arm 13 are first rotated in parallel by the same angle (namely, the difference between the states before and after the retraction operation) and then the first arm 11 is moved more than that angle is canceled. Furthermore, a determination as to whether the restoration operation can be performed may be made when the distance between the first apparatus 11 and the second apparatus 13 exceeds a predetermined value. In this case, the restoration operation is started based on the result of determination. Furthermore, the restoration operation may be performed using the position detected before retraction, when the distance between the first apparatus 11 and the second apparatus 13 exceeds a predetermined value. The restoration operation may be executed based on entered operation instructions.

Step S23 (which determines whether or not the retraction operation can be performed) need not be performed when the first arm 11 moves to a position within a predetermined distance of the second arm 13. That is, step S23 may be performed when the distance between the first arm 11 and the second arm 13 becomes smaller than a predetermined value.

The term "processor" used in the above descriptions is intended to cover, for example, a dedicated or general-purpose processor, a circuit (circuitry), a processing circuit (circuitry), an operation circuit (circuitry), or an arithmetic circuit (circuitry); alternatively, the "processor" may include the following types of circuit: an application-specific integrated circuit (ASIC), a simple programmable logic device (SPLD), a complex programmable logic device (CPLD), a field programmable gate array (FPGA), or the like. In addition, each of the structural elements (processors) of the present embodiment is not limited to a single processor but may be attained by a plurality of processors. In addition, some of the structural elements (processors) of the present embodiment may be attained by a single processor.

While certain embodiments have been described, these embodiments have been presented by way of example only, and are not intended to limit the scope. Indeed, the novel methods and systems described herein may be embodied in a variety of other forms; furthermore, various omissions, substitutions, and changes in the form of the methods and systems described herein may be made without departing from the spirit. The accompanying claims and their equivalents are intended to cover such forms or modifications as would fall within the scope and spirit.

What is claimed is:

1. An X-ray diagnostic apparatus comprising:
   a first apparatus located in an examination room and used for X-ray diagnosis;
   a second apparatus located in the examination room and used for X-ray diagnosis;
   movement instruction input circuitry configured to input a movement instruction for moving the first apparatus to a target position; and
   control circuitry configured to control the first apparatus and the second apparatus in accordance with the movement instruction, such that the first apparatus is moved to the target position,
   wherein the control circuitry is configured to execute (i) a retraction operation in which the first apparatus starts moving toward the target position in response to the movement instruction and continues to move toward the target position, with the second apparatus retracted, and (ii) a restoration operation in which the second apparatus is returned to a position before the retraction operation, while avoiding collision with the first apparatus.

2. The X-ray diagnostic apparatus according to claim 1, wherein the control circuitry is configured to start the restoration operation when a relationship between the first apparatus and the second apparatus satisfies a predetermined condition.

3. The X-ray diagnostic apparatus according to claim 1, further comprising:
   retraction operation determination circuitry configured to determine whether or not the retraction operation can be performed, when a distance between the first apparatus and the second apparatus becomes less than a predetermined value.

4. The X-ray diagnostic apparatus according to claim 1, wherein the control circuitry is configured to determine whether the restoration operation can be performed when a distance between the first apparatus and the second apparatus exceeds a predetermined value, and start the restoration operation based on a result of determination.

5. The X-ray diagnostic apparatus according to claim 1, further comprising:
   position detection circuitry configured to detect a position of the second apparatus,
   wherein the control circuitry configured to perform the restoration operation using the position detected before retraction, when a distance between the first apparatus and the second apparatus exceeds a predetermined value.

6. The X-ray diagnostic apparatus according to claim 1, further comprising:
   a detector configured to detect whether or not there is an obstacle between the position where the second apparatus is located before retraction and the position where the second apparatus is located when the first apparatus has reached the target position.

7. The X-ray diagnostic apparatus according to claim 1, wherein the first apparatus is one of an arm, a monitor table, a bed and a top plate.

8. The X-ray diagnostic apparatus according to claim 1, wherein the second apparatus is one of an arm, a monitor table, a bed and a top plate.

9. The X-ray diagnostic apparatus according to claim 1, wherein the first apparatus is a first arm which supports a first X-ray tube and a first X-ray detector, and
   the second apparatus is a second arm which supports a second X-ray tube and a second X-ray detector.

10. The X-ray diagnostic apparatus according to claim 9, further comprising:
    position detection circuitry configured to detect a position of the second apparatus,
    wherein the position detected by the position detection circuitry is defined by a rotating angle of the second arm.

11. The X-ray diagnostic apparatus according to claim 9, wherein the control circuitry is configured to control the second arm to return the second arm to the position where the second arm is located before retraction, when the second X-ray tube is not performing irradiation or is not ready for irradiation.

12. The X-ray diagnostic apparatus according to claim 1, further comprising:
    retraction operation determination circuitry configured to determine whether or not the retraction operation can be performed, when the first apparatus and the second apparatus move closer to each other and are within a predetermined distance.

13. The X-ray diagnostic apparatus according to claim 1, wherein the control circuitry is configured to start the restoration operation when an operation of the first apparatus ends.

14. The X-ray diagnostic apparatus according to claim 13, further comprising:
stop input circuitry configured to input an instruction for stopping the restoration operation after the restoration is started.

15. The X-ray diagnostic apparatus according to claim 14, wherein the control circuitry is configured to cancel the restoration operation and move the second apparatus to the position where the second apparatus is located when the restoration processing is started, when the instruction for stopping the restoration operation is entered from the stop input device.

16. The X-ray diagnostic apparatus according to claim 14, wherein the control circuitry is configured to cancel the restoration operation and cause the second apparatus to remain on a spot, when the instruction for stopping the restoration operation is entered from the stop input device.

17. The X-ray diagnostic apparatus according to claim 9, wherein the control circuitry is configured to cancel the restoration operation and cause the second apparatus to remain on a spot, when the second X-ray tube starts emitting X-rays after the restoration operation is started.

18. The X-ray diagnostic apparatus according to claim 13, further comprising:
memory circuitry configured to store priorities and apparatuses, including to the first apparatus and the second apparatus, in association with each other, wherein the priorities indicate that the restoration operation cannot be executed if the second apparatus has a priority higher than that of the first apparatus and that the restoration operation can be executed when the second apparatus has a priority equal to or lower than that of the first apparatus,
wherein the control circuitry is configured to retract the second apparatus while maintaining a predetermined distance to the first apparatus, when the first apparatus starts moving in response to the movement instruction and reaches a position within the predetermined distance of the second apparatus, and execute the restoration operation in accordance with the priorities when the first apparatus reaches the target position.

19. The X-ray diagnostic apparatus according to claim 13, wherein the restoration operation is an operation in which the second apparatus is returned to the position before retraction, using a route followed by the second apparatus.

20. The X-ray diagnostic apparatus according to claim 13, further comprising:
calculation circuitry configured to calculate times corresponding to a plurality of routes through which the second arm device can be returned from the position where the second apparatus is located when the first apparatus has reached the target position to the position where the second apparatus is located before retraction; and
determination circuitry configured to determine a route requiring a shortest time,
wherein the restoration operation is an operation in which the second apparatus is returned, using the route requiring the shortest time.

* * * * *